United States Patent
Kuroda et al.

(10) Patent No.: US 9,695,148 B2
(45) Date of Patent: Jul. 4, 2017

(54) 2-PYRIDONE COMPOUND

(71) Applicants: TAISHO PHARMACEUTICAL CO., LTD., Tokyo (JP); NISSAN CHEMICAL INDUSTRIES, LTD., Tokyo (JP)

(72) Inventors: Shoichi Kuroda, Tokyo (JP); Yudai Imai, Tokyo (JP); Takanori Kawaguchi, Tokyo (JP); Keiko Fusegi, Tokyo (JP); Masahiro Bohno, Tokyo (JP); Hajime Asanuma, Tokyo (JP); Tomomichi Chonan, Tokyo (JP); Nagaaki Sato, Saitama (JP); Souichi Monma, Funabashi (JP); Shigetada Sasako, Funabashi (JP); Marie Mizutani, Funabashi (JP); Shin Itoh, Funabashi (JP); Takumi Okada, Funabashi (JP); Hirofumi Ota, Funabashi (JP); Seishi Ishiyama, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 16 days.

(21) Appl. No.: 14/442,157

(22) PCT Filed: Nov. 12, 2013

(86) PCT No.: PCT/JP2013/080517
§ 371 (c)(1),
(2) Date: May 12, 2015

(87) PCT Pub. No.: WO2014/077235
PCT Pub. Date: May 22, 2014

(65) Prior Publication Data
US 2016/0289208 A1   Oct. 6, 2016

(30) Foreign Application Priority Data
Nov. 13, 2012   (JP) .................... 2012-249792

(51) Int. Cl.
*C07D 401/06* (2006.01)
*A61K 31/4439* (2006.01)

(52) U.S. Cl.
CPC ........ *C07D 401/06* (2013.01); *A61K 31/4439* (2013.01)

(58) Field of Classification Search
CPC .................... C07D 401/06; A61K 31/4439
See application file for complete search history.

(56) References Cited

U.S. PATENT DOCUMENTS

| 4,275,069 A | 6/1981 | Youngdale |
| 8,822,503 B2* | 9/2014 | Kawaguchi .......... C07D 213/64 514/343 |
| 2011/0237791 A1 | 9/2011 | Kawaguchi et al. |

FOREIGN PATENT DOCUMENTS

| JP | 2013-10750 A | 1/2013 |
| WO | 00/58293 A2 | 10/2000 |
| WO | 01/44216 A1 | 6/2001 |
| WO | 2008/079787 A2 | 7/2008 |
| WO | 2010/013161 A1 | 2/2010 |
| WO | 2011/068211 A1 | 6/2011 |

OTHER PUBLICATIONS

Tura Ferre, et al., "Correction of diabetic alterations by glucokinase", Proceedings of the National Academy of Sciences of the United States of America, Jul. 9, 1996, pp. 7225-7230, vol. 93, No. 14.
Benjamin Glaser, M.D., et al., "Familial Hyperinsulinism Caused by an Activating Glucokinase Mutation", The New England Journal of Medicine, Jan. 22, 1998, pp. 226-230, vol. 338, No. 4.
Andrew Grupe, et al., "Transgenic Knockouts Reveal a Critical Requirement for Pancreatic β Cell Glucokinase in Maintaining Glucose Homeostasis", Cell, Oct. 6, 1995, pp. 69-78, vol. 83, No. 1.
Ling Kang, et al., "Glucokinase is a Critical Regulator of Ventromedial Hypothalamic Neuronal Glucosensing", Diabetes, Feb. 2006, pp. 412-420, vol. 55, No. 2.
Latif Rateb, et al., "Reactions of Hydroxymethylene Ketones. Part III.1 Synthesis of 1,2-Dihydro-2-oxo-pyridine Polycarboxylic Acids", The Journal of the Chemical Society, 1968, pp. 2140-2144, vol. 17.

(Continued)

*Primary Examiner* — D M Seaman
(74) *Attorney, Agent, or Firm* — Sughrue Mion, PLLC (57) ABSTRACT

This 2-pyridone compound represented by formula [1] or a tautomer of said compound, or a pharmaceutically acceptable salt of said compound or said tautomer, or a solvate of said compound or the like has a superior GK-activating effect and is useful as a pharmaceutical.

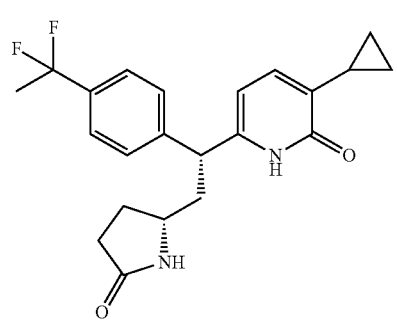

[1]

8 Claims, 3 Drawing Sheets

(56) References Cited

OTHER PUBLICATIONS

Mark A. Magnuson, et al., "Glucokinase as a Glucose Sensor: Past, Present and Future", Diabetes, 2004, pp. 1-15, 34-35, vol. 16.

F.M. Matschinsky, et al., "Glucokinase and Glycemic Disease; From Basics to Novel Therapeutics", Frontiers in Diabetes, 2004, pp. 1, vol. 16.

N. Vionnet, et al., "Nonsense mutation in the glucokinase gene causes early-onset non-insulin-dependent diabetes mellitus", Nature, International Weekly Journal of Science, Apr. 23, 1992, pp. 721-722, vol. 356, No. 6371.

International Search Report of PCT/JP2013/080517, dated Feb. 10, 2014. [PCT/ISA/210].

* cited by examiner

2-PYRIDONE COMPOUND

CROSS REFERENCE TO RELATED APPLICATIONS

This application is a National Stage of International Application No. PCT/JP2013/080517 filed Nov. 12, 2013, claiming priority based on Japanese Patent Application No. 2012-249792, filed Nov. 13, 2012, the contents of all of which are incorporated herein by reference in their entirety.

TECHNICAL FIELD

The present invention relates to novel 2-pyridone compounds having a glucokinase activating effect and to a medicine comprising the compound as an active ingredient. Further, the present invention relates to the crystals of the compounds and a method for producing the same.

BACKGROUND ART

The number of patients suffereing from type II diabetes is increasing worldwide, and progress of the patient's conditions and development of the complication cause a severe prognosis, under which the circumstances the development of a novel prophylactic agent or a therapeutic agent is eagerly desired. Type II diabetes, with the background of genetic predisposition and aging suggested to be associated with the development thereof, is considered to have a significantly increased risk of the development when the life style common in developed countries, namely, the condition involving an excessive energy intake to physical activities, is imposed. Also, the metabolic disorders, which are the underlying conditions, include poor glucose utilization in the skeletal muscle and fat tissues, insulin secretion disorder from pancreatic beta cells, and insufficient control of glucose release from the liver and an agent to improve these disorders is considered to be useful for preventing and treating type II diabetes.

For the glucose utilization in the skeletal muscle and fat tissues, a drug therapy using insulin sensitizers represented by a thiazolidine derivative (e.g., pioglitazone) is considered to be effective; however, aggravated obesity, body fluid retention, increased risk of cardiac insufficiency, increased incidence of bladder cancer, and the like, have been reported, where careful assessment is hence required when using these drugs. Further, for the insulin secretion disorder, sulfonylurea drugs (e.g., glimepiride, glibenclamide, glipizide) are considered to be effective; however, hypoglycemia and/or overweight is often caused, and also poor blood glycemic control (secondary failure) may occur due to reduced therapeutic effects when used for an extended period of time, thus leaving both safety and efficacy issues to be resolved. For the postprandial hyperglycemia, α-glucosidase inhibitors (e.g., acarbose, voglibose, and miglitol), or glinide drugs (e.g., nateglinide, repaglinide, and mitiglinide) are used but have limited therapeutic effects on diabetes. For controlling the glucose release from the liver, biguanide drugs (e.g., metformin) are effective, but glycemic control becomes difficult as conditions progress and additionally, in some cases, use of the drug may be limited due to the adverse effects on the digestive tract, lactic acidosis risk, or the like. As evident from the findings of the above major agents, the existing agents do not necessarily meet the medical requirements. In particular, metformin is substantially the only agent for directly improving the liver glucose metabolism, under which circumstance it is extremely essential to develop an agent capable of improving the liver glucose metabolism by a novel mechanism of action.

Glucokinase (hereinafter described as GK) belongs to the hexokinase family and catalyzes phosphorylation of glucose incorporated in cells such as pancreatic beta cells or hepatocytes. GK in the liver and pancreatic beta cells differ from each other in terms of the sequence of N-terminal 15 amino acids due to the difference in splicing but are enzymatically identical. GK has a high affinity to glucose $S_{0.5}$ of about 10 mM and is not inhibited by the product, glucose 6-phosphate. Therefore, its reaction rate sensitively responds to physiological changes of blood glucose levels. GK in pancreatic beta cells modulates glucose-dependent insulin secretion, while GK in the liver modulates the glycolytic pathway or glycogenesis, so that blood glucose levels are maintained and controlled. Therefore, GK is assumed to function as a glucose sensor to maintain homeostasis of blood glucose levels (see Non Patent Literature 1).

Genetically engineered mice and gene mutations discovered in humans support a hypothesis that GK functions as an in vivo glucose sensor. GK homozygous mice have been died of hyperglycemia immediately after birth, and heterozygous mice have been observed to have hyperglycemia and impaired glucose tolerance (see Non Patent Literature 2). In contrast, GK overexpressed mice have been confirmed to have hypoglycemia (see Non Patent Literature 3). Moreover, in human MODY2 (maturity onset diabetes of the young), in which GK gene mutation is observed, diabetes develops from his youth (see Non Patent Literature 4). These gene mutations have been confirmed to reduce GK activity. In contrast, families have been reported having gene mutations to enhance GK activity (see Non Patent Literature 5). These gene mutations have been observed to enhance affinity of GK to glucose and cause symptoms of fasting hypoglycemia associated with elevated blood insulin concentrations.

In this way, GK has been shown to function as a glucose sensor in mammals including humans.

Substances to increase GK activity (hereinafter described as GK activating substances) may improve hyperglycemia by increasing glucose metabolism and glycogenesis in the liver and glucose-responsive insulin secretion from pancreatic beta cells. In particular, the substances which increase GK activity predominantly in the liver may improve hyperglycemia by promoting the glucose metabolism in the liver in an insulin-independent manner. It can also expected that improvement of hyperglycemia leads to treatment and prevention of chronic diabetic complications such as retinopathy, nephropathy, neurosis, ischemic heart disease and arteriosclerosis and to treatment and prevention of diabetes-related diseases such as obesity, hyperlipidemia, hypertension and metabolic syndrome. Therefore, compounds to increase the function of GK are expected to be effective therapeutic agents for diabetes.

On the other hand, GK has been reported to be expressed not only in the pancreas and liver but also in the feeding center and to have an important function in the antifeeding effect by glucose (see Non Patent Literature 6). Accordingly, GK activating substances may act on the feeding center and have an antifeeding effect and can be expected not only as therapeutic agents for diabetes but also as therapeutic agents for obesity.

Incidentally, some compounds having 2-pyridone are reported as the GK activating substances but they are structurally far removed from those of the present invention (see Patent Literatures 1 and 2). Other 2-pyridone compounds having closely related structures are reported but the compounds of the present invention are not disclosed specifically (see Patent Literatures 3 and 4). The present invention differs from the report in that the report contains no description regarding the medical application and that it rather focuses on a synthetic method of 2-pyridone compounds (see Non Patent Literature 7). Further, certain acylurea compounds that may have a pseudocyclic structure have been reported as GK activating substances, but they are noncyclic compounds and differ from the compounds of the present invention (see Patent Literatures 5 and 6).

CITATION LIST

Non Patent Literature

Non Patent Literature 1: Matschinsky F. M. and Magnuson M. A., Frontiers in Diabetes, 16, 2004
Non Patent Literature 2: Grupe A. et al. Cell, 83, 1, 69-78, 1995
Non Patent Literature 3: Ferre T. et al. Proc. Natl, Acad. Sci., 93, 14, 7225-7230, 1996
Non Patent Literature 4: Vionnet N. et al. Nature, 356, 6371, 721-722, 1992
Non Patent Literature 5: Glaser B. et al. N. Engl. J. Med. 338, 4, 226-230, 1998
Non Patent Literature 6: Kang L. et al, Diabetes, 55, 2, 412-420, 2006
Non Patent Literature 7: Latif R. et al. J. Chem. Soc. C. Organic, 17, 2140-2144, 1968

Patent Literature

Patent Literature 1: WO 2008/079787
Patent Literature 2: WO 2010/013161
Patent Literature 3: US 4275069
Patent Literature 4: WO 2011/068211
Patent Literature 5: WO 2000/58293
Patent Literature 6: WO 2001/44216

SUMMARY OF INVENTION

Technical Problem

An object of the present invention is to provide compounds that have an excellent GK activating effect and are useful as pharmaceuticals.

Solution to Problem

In view of the circumstances mentioned above, the present inventors have carried out extensive studies to find compounds having a GK activating effect and, as a result, have found that the object can be achieved by a 2-pyridone compound represented by the following formula [1] (compound name: 3-cyclopropyl-6-{(1R)-1-[4-(1,1-difluoroethyl)phenyl]-2-[(2R)-5-oxopyrrolidin-2-yl]ethyl}pyridin-2(1H)-one), a tautomer of the compound, a pharmaceutically acceptable salt thereof (hereinafter the 2-pyridone compound, a tautomer of the compound, or a pharmaceutically acceptable salt thereof is represented by the term "the 2-pyridone compound or the relatives"), or a solvate of the 2-pyridone compound or the relatives, whereby the present invention has been accomplished.

(I) An embodiment of the present invention provides a 2-pyridone compound represented by formula [1]:

[Formula 1]

[1]

a tautomer of the compound, a pharmaceutically acceptable salt thereof, or a solvate of the 2-pyridone compound or the relatives.

(II) Another embodiment of the present invention provides a crystal of 3-cyclopropyl-6-{(1R)-1-[4-(1,1-difluoroethyl)phenyl]-2-[(2R)-5-oxopyrrolidin-2-yl]ethyl}pyridin-2(1H)-one according to (I), represented by the above formula [1] and having a physical property of the following (a):
(a) an X-ray powder diffraction pattern (Cu—Kα) showing peaks at diffraction angles 2θ of 8.5, 13.4, 19.1 and 24.5°.

(III) Another embodiment of the present invention provides a crystal of 3-cyclopropyl-6-{(1R)-1-[4-(1,1-difluoroethyl)phenyl]-2-[(2R)-5-oxopyrrolidin-2-yl]ethyl}pyridin-2(1H)-one according to (I), represented by the above formula [1] and having physical properties of the following (a) to (c):
(a) an X-ray powder diffraction pattern (Cu—Kα) showing peaks at diffraction angles 2θ of 8.5, 13.4, 19.1 and 24.5°;
(b) an infrared absorption spectrum showing characteristic absorption bands at 916, 1146, 1167, 1295, 1651, 1664, 2909, 2955, 3003 and 3146 $cm^{-1}$; and
(c) a melting point of 199 to 201° C.

(IV) Another embodiment of the present invention provides a method for producing a crystal of 3-cyclopropyl-6-{(1R)-1-[4-(1,1-difluoroethyl)phenyl]-2-[(2R)-5-oxopyrrolidin-2-yl]ethyl}pyridin-2(1H)-one having the physical properties of the following (a) to (c):
(a) an X-ray powder diffraction pattern (Cu—Kα) showing peaks at diffraction angles 2θ of 8.5, 13.4, 19.1 and 24.5°;
(b) an infrared absorption spectrum showing characteristic absorption bands at 916, 1146, 1167, 1295, 1651, 1664, 2909, 2955, 3003 and 3146 $cm^{-1}$; and
(c) a melting point of 199 to 201° C.,
the method comprising: dissolving 3-cyclopropyl-6-{(1R)-1-[4-(1,1-difluoroethyl)phenyl]-2-[(2R)-5-oxopyrrolidin-2-yl]ethyl}pyridin-2(1H)-one represented by the above formula [1] in an alcohol solvent while heating, to provide a solution; thereafter, adding a water solvent to the solution; cooling the resultant solution to 5° C. or lower to yield a crystal; and drying the obtained crystal at 60° C. or lower.

(V) Another embodiment of the present invention provides a medicine comprising, as an active ingredient, the 2-pyridone compound, a tautomer of the compound, a pharmaceutically acceptable salt thereof, or a solvate of the 2-pyridone compound or the relatives according to (I).

(VI) Another embodiment of the present invention provides the medicine according to (V), wherein the medicine is used for preventing or treating a disease or condition that can be improved by a glucokinase activating effect.

(VII) Another embodiment of the present invention provides the medicine according to (V), which is a hypoglycemic agent.

(VIII) Another embodiment of the present invention provides the medicine according to (V), wherein the medicine is a prophylactic or therapeutic agent for diabetes.

Advantageous Effects of Invention

According to the present invention, there were provided 2-pyridone compounds having an excellent GK activating effect.

Moreover, according to the present invention, there was provided the crystal of 3-cyclopropyl-6-{(1R)-1-[4-(1,1-difluoroethyl)phenyl]-2-[(2R)-5-oxopyrrolidin-2-yl]ethyl}pyridin-2(1H)-one, which has a novel crystal useful as a pharmaceutical. The crystal is in the stable crystal form at around room temperature and has good storage stability.

Furthermore, according to the present invention, there was provided a novel production method for yielding the above crystal in a uniform quality in a safe and stable manner.

DESCRIPTION OF EMBODIMENTS

The present invention will be described in detail below, but is not particularly limited to the exemplified embodiments.

In the present invention, "n" refers to normal, "i" refers to iso, "s" and "sec" refer to secondary, "tert" refers to tertiary, "c" refers to cyclo, "o" refers to ortho, "m" refers to meta and "p" refers to para.

First, the compounds of the present invention are described.

Examples of the pharmaceutically acceptable salts in the present invention include mineral acid salts such as hydrochlorides, hydrobromides, hydroiodides, phosphates, sulfates and nitrates; sulfonates such as methanesulfonates, ethanesulfonates, benzenesulfonates and p-toluenesulfonates; carboxylates such as oxalates, tartrates, citrates, maleates, succinates, acetates, benzoates, mandelates, ascorbates, lactates, gluconates and malates; amino acid salts such as glycine salts, lysine salts, arginine salts, ornithine salts, glutamates and aspartates; and mineral salts such as lithium salts, sodium salts, potassium salts, calcium salts and magnesium salts, and salts with organic bases such as ammonium salts, triethylamine salts, diisopropylamine salts and cyclohexylamine salts. Preferred examples include hydrochlorides, hydrobromides, phosphates, sulfates, methanesulfonates, p-toluenesulfonates, oxalates, tartrates, citrates, acetates, lactates, glutamates, aspartates, sodium salts, potassium salts, ammonium salts and triethylamine salts.

The solvates in the present invention are pharmaceutically acceptable solvates of the compounds or salts thereof of the present invention. The compounds and salts thereof of the present invention may absorb moisture, have adsorbed water, or form hydrates by exposure to the air, recrystallization or the like. The compounds of the present invention also include such hydrates.

The compounds of the present invention have two asymmetric centers and are optically active compounds, and the absolute configuration of both of the two asymmetric centers of the present compounds is (R). The compounds of the present invention can be obtained by the optical resolution of the corresponding racemic or diastereomer mixture. The optical resolution methods adoptable include those well known to a person skilled in the art such as fractional crystallization method or chiral column chromatography. Alternatively, the optically active compounds of the present invention can also be obtained by a well known technique in organic chemistry practiced for this purpose. Further, geometrical isomers such as (E) isomer and (Z) isomer may be present as the synthetic intermediates for obtaining the compounds of the present invention, and the ratio of these isomers can be in any proportion.

The compounds of the present invention encompass tautomers. The tautomer herein refers to a keto-enol tautomer of the compounds represented by the above formula [1].

The compounds represented by the above formula [1] and the tautomer [1'] thereof are shown below as an example.

[Formula 2]

The 2-pyridone compounds of the present invention may be pharmaceutically acceptable salts thereof or solvates of the 2-pyridone compound or the relatives. Hereinafter, the 2-pyridone compounds, tautomers of the compounds, pharmaceutically acceptable salts thereof, or solvates of the 2-pyridone compound or the relatives are collectively referred to as the "compounds of the present invention".

The "compounds of the present invention" also include compounds commonly called prodrugs which have a chemically or metabolically decomposable group and form the pharmacologically active compounds of the present invention by solvolysis or in vivo under physiological conditions.

The compounds of the present invention have a GK activating effect. Therefore, the compounds of the present invention can improve hyperglycemia by increasing glucose metabolism mainly in the liver. Accordingly, the compounds can be used as novel drug therapies that differ in mechanism of action from the existing therapeutic agents for diabetes. Diabetes include type I diabetes, type II diabetes and other diabetes due to specific causes. The compounds of the present invention are also effective for the treatment and prevention of diabetic complications such as ketoacidosis, microangiopathy (retinopathy or nephropathy), arteriosclerosis (such as atherosclerosis, myocardial infarction, cerebral infarction or peripheral arterial occlusive disease), neuropathy (such as sensory neuropathy, motor neuropathy or autonomic neuropathy), foot gangrene and infections.

The compounds can also be used for the treatment and prevention of diabetes-related diseases such as obesity, hyperlipidemia, hypertension, metabolic syndrome, edema, hyperuricemia and gout.

The compounds of the present invention can also be used in combination with therapeutic agents having a mechanism of action other than a GK activating effect, such as those for diabetes, diabetic complications, hyperlipidemia, hypertension and the like. By combining the compounds of the present invention with those other agents, an additive effect can be expected for the above diseases as compared with the effect achieved by those respective agents each alone.

Examples of the therapeutic agents for diabetes and the therapeutic agents for diabetic complications usable in combination with the compounds of the present invention include insulin preparations, insulin sensitizers (such as PPARγ agonists, PPARα/γ agonists, PPARδ agonists and PPARα/γ/δ agonists) (e.g., pioglitazone, rosiglitazone, aleglitazar, peliglitazar, AVE-0897 and MBX-8025), α-glucosidase inhibitors (e.g., voglibose, acarbose and miglitol), biguanide drugs (e.g., metformin, buformin and phenformin), insulin secretion promoters (e.g., glibenclamide, glimepiride, repaglinide, nateglinide and mitiglinide), glucagon receptor antagonists, insulin receptor kinase promoters, dipeptidyl peptidase IV inhibitors (e.g., vildagliptin, alogliptin, sitagliptin, linagliptin, saxagliptin, teneligliptin, anagliptin), SGLT inhibitors (e.g., dapagliflozin, luseogliflozin, canagliflozin, empagliflozin, ipragliflozin, tofogliflozin), PTP1b inhibitors (e.g., sodium vanadate), glucose 6-phosphatase inhibitors, glycogen phosphorylase inhibitors (e.g., PSN-357 and FR-258900), FBPase inhibitors (e.g., MB-07803), PEPCK inhibitors, pyruvate dehydrogenase kinase inhibitors, D-chiro-inositol, GSK3 inhibitors, GLP-1 agonists (e.g., liraglutide and exenatide), amylin agonists (e.g., pramlintide), glucocorticoid receptor antagonists, 11βHSD1 inhibitors (e.g., INCB-13739, LY-2523199, Ro-5027838, Ro-5093151 and S-707106), protein kinase C inhibitors (e.g., ruboxistaurin), β3 adrenaline receptor agonists, phosphatidylinositol kinase inhibitors, phosphatidylinositol phosphatase inhibitors, ACC inhibitors, GPR40 receptor agonists (e.g., TAK-875), GPR119 receptor agonists (e.g., APD-597, PSN-821, MBX-2982 and DS-8500), GPR120 receptor agonists, TGR5 receptor agonists, AMPK activators, aldose reductase inhibitors (e.g., epalrestat, ranirestat, fidarestat) and AGE inhibitors.

Also, examples of the agents for diabetes-related diseases usable in combination with the compounds of the present invention include HMG-CoA reductase inhibitors, squalene synthase inhibitors, bile acid adsorbents, IBAT inhibitors, CETP inhibitors, CPT inhibitors, fibrates, ACAT inhibitors, MGAT inhibitors, DGAT inhibitors, cholesterol absorption inhibitors, pancreatic lipase inhibitors, MTP inhibitors, nicotinic acid derivatives, LXR agonists, LDL receptor promoters, angiotensin-converting enzyme inhibitors, angiotensin II antagonists, renin receptor antagonists, aldosterone antagonists, diuretics, calcium antagonists, alpha-blockers, beta-blockers,endothelin-converting enzyme inhibitors, endothelin receptor antagonists, appetite suppressants, uric acid production inhibitors and uricosuric agents.

The compounds of the present invention can be administered alone or with pharmaceutically or pharmacologically acceptable carriers or diluents. The compounds of the present invention used as GK activating substances may be orally or parenterally administered as such. The compounds of the present invention may also be orally or parenterally administered as agents containing the compounds as active ingredients. Examples of the parenteral administration include intravenous administration, nasal administration, transdermal administration, subcutaneous administration, intramuscular administration and sublingual administration.

The dosage of the compound of the present invention varies depending on the subject of administration, the route of administration, the disease of interest, the symptom and the like, and is usually about 0.01 to 1000 mg, and preferably 0.1 to 100 mg as a single dose when orally administered to an adult patient with diabetes, for example; it is desirable to administer this dose once, twice or three times per day.

Next, the method for producing the compounds of the present invention is described.

The compounds of the present invention can be synthesized by the processes shown below. The following production processes show general examples of production processes and do not limit the production processes.

The compounds of the present invention may also be synthesized using a method known in the field of chemistry per se or a method through one or more processes similar to that method. Examples of such methods include methods described in Organic Functional Group Preparations, 2nd ed., Academic Press, Inc., 1986, Comprehensive Organic Transformations, VCH Publishers Inc., 1989 and Fundamentals and Experiments of Peptide Synthesis, Maruzen Co., Ltd., 1985.

Suitable methods of protection and deprotection of functional groups contained in the starting materials, intermediates or the like in the synthesis of the compounds of the present invention can be performed according to the methods well known to a person skilled in the art such as the methods described in Greene's Protective Groups in Organic Synthesis, John Wily and Sons, 2006.

General processes for producing the compounds of the present invention are shown in Schemes 1 to 2. The following production processes do not limit the production processes. The compounds of the present invention can also be produced by using the methods well known to a person skilled in the art, for example, by changing the order of performing the steps; providing a protecting group for a hydroxy group or the like, carrying out a reaction and deprotecting in the subsequent step; or adding a new step in the course of respective steps.

Scheme 1: Process for synthesizing compound [1] of the present invention from compound (1-a).

Step (1-1):

Method for producing compound (1-b): the compound (1-b) can be produced by performing "fluorination" using a fluorinating reagent such as N,N-dimethoxyethylaminosul-

[Formula 3]

(wherein in the scheme, $G^1$ represents a protecting group for the hydroxy group in the hydroxypyridyl group, $R^1$ represents a 2-benzothiazolyl group or 1-phenyl-1H-tetrazol-5-yl group.)

The compound (1-g) used in the step (1-4) may be obtained as a commercially available compound, a commonly known compound, or a compound easily obtainable using a variety of organic synthesis techniques known to a person skilled in the art.

fur trifluoride (bis(2-methoxyethyl)aminosulfur trifluoride or Deoxo-Fluor (registered trademark)).

Examples of the fluorination include a method in which a fluorinating reagent such as Deoxo-Fluor (registered trademark) is reacted with the compound (1-a) in the absence of a solvent or in an inert solvent at a temperature of 0° C. to 100° C. to produce the compound (1-b).

Step (1-2):

Method for producing compound (1-d): the compound (1-d) can be produced by reacting the compound (1-c) with the compound (1-b) in an inert solvent in the presence of a base such as potassium acetate and a palladium catalyst.

Step (1-3):

Method for producing compound (14 the compound (1-0 can be produced by reacting a base such as n-butyllithium or n-butylmagnesium chloride with the compound (1-e) in an inert solvent and subsequently reacting N,N-dimethylformamide therewith.

The compound (1-e), a starting substance, can be obtained by the method described in WO 2011/068211 or a method in accordance therewith.

Steps (1-4, 1-5):

Method for producing compound (1-h): the compound (1-h) can be produced by reacting in an inert solvent bromine with (5R)-5[2-(5-cyclopropyl-6-methoxypyridin-2-yl)ethenyl]pyrrolidin-2-one (an E/Z mixture) obtained by a "coupling reaction" using the carbonyl compound (1-0 and the compound (1-g), and subsequently reacting a base such as 1,8-diazabicyclo[5.4.0]undec-7-ene (DBU) therewith.

Examples of the "coupling reaction" include a method for providing a compound (1-h) by generating an anion using the compound (1-g) as a matrix and an organometallic reagent such as n-butyllithium, sec-butyllithium or tert-butyllithium or a base such as lithium hexamethyldisilazide or potassium hexamethyldisilazide at a temperature of −78° C. to 100° C. in an inert solvent and then reacting the anion with a carbonyl compound (1-f). The olefin compound to be obtained is typically obtained in the form of E/Z mixtures, which however can be isolated respectively by resolution using silica gel column chromatography or HPLC.

The compound (1-g) used for the coupling reaction can be obtained by the method described in WO 2011/068211 or a method in accordance therewith.

Step (1-6):

Method for producing compound (1-i): the compound (1-i) can be produced by performing "coupling reaction" with the phenyl boron compound (1-d) using the compound (1-h) as a matrix in the presence of a palladium catalyst.

Examples of the coupling reaction include a method for reacting the compound (1-h) and the phenyl boron compound in an inert solvent at a temperature of 20° C. to 160° C. in the presence of a palladium catalyst and a base. The reaction can also be carried out by using microwaves.

Examples of the palladium catalyst used for the coupling reaction include palladium catalysts known to a person skilled in the art such as tetrakistriphenylphosphine palladium(0), bis(dibenzylideneacetone)palladium(0), tris(dibenzylideneacetone)dipalladium(0), bis(triphenylphosphine) palladium(II) dichloride, bis(triphenylphosphine)palladium (II) acetate and a [1,1'-bis(diphenylphosphino)ferrocene] palladium(II) dichloride-dichloromethane complex (1:1). Also, in the presence of a base, tris(dibenzylideneacetone) dipalladium(0) and tri(2-furyl)phosphine can be used for the reaction.

Step (1-7):

Method for producing compound (1-j): the compound (1-j) can be produced by reducing the compound (1-i) as a matrix by a catalytic hydrogenation reaction with a catalytic amount of palladium-activated carbon, rhodium-activated carbon or platinum-activated carbon in an inert solvent in the presence or absence of an acid at a temperature of 0° C. to 80° C.

Step (1-8):

Method for producing compound (1-k): the compound (1-k) can be produced by performing "deprotection reaction" of the protecting group $G^1$ possessed by a compound (1-j).

Examples of the deprotection reaction include (i) deprotection reactions where the protecting group $G^1$ is an alkyl group or an allyl group, such as a method of removing the protecting group by hydrolysis reaction in an inert solvent in the presence of an acid or a strong acid at a temperature of 0° C. to 200° C., a method using trimethylsilyl iodide, or the like, and a method using aluminum chloride and alkylthiol, and (ii) deprotection reactions where the protecting group $G^1$ is a benzyl group, a 4-methoxybenzyl group, a 2,4-dimethoxybenzyl group, a benzyloxycarbonyl group, a benzhydryl (diphenylmethyl) group or the like, such as a method of removing the protecting group by hydrogenolysis reaction using a catalytic amount of palladium-activated carbon, rhodium-activated carbon or the like in an inert solvent in the presence or absence of an acid at a temperature of 0° C. to 80° C., or a method using an oxidizing agent such as ammonium cerium(IV) nitrate or 2,3-dichloro-5,6-dicyano-p-benzoquinone.

Step (1-9):

Method for obtaining the compound [1] of the present invention: the compound [1] of the present invention can be obtained by diastereomeric resolution of compound (1-k) using, for example, HPLC.

The compound (1-a) and the compound (1-c) used as the raw material compounds in the above Scheme 1 can be obtained as commercial products or by a known method.

Scheme 2: Process for synthesizing the compound [1] of the present invention from compound (2-a)

[Formula 4]

(wherein in the scheme, $G^1$ and $R^1$ are as defined above. $G^2$ represents a protecting group for the nitrogen atom in the pyrrolidinyl group substituted with an oxo group.)

Step (2-1):

Method for producing compound (2-b): the compound (2-b) can be obtained by the method described in WO 2008/103185 or a method in accordance therewith.

Steps (2-2, 2-3):

Method for producing compound (2-c): the compound (2-c) can be produced by performing "addition reaction" using the compound (2-b) and an anion such as a lithium reagent such as heteroaryl lithium, a Grignard reagent such as heteroaryl magnesium bromide, and treating the obtained compound with an acid such as hydrochloric acid.

Examples of the "addition reaction" include a method for reacting the compound (2-b) with an anion generated by using the compound (1-e) as a matrix and an organometallic reagent such as n-butyllithium, sec-butyllithium, tert-butyllithium, or isopropyl magnesium bromide, a metal reagent such as magnesium or a base such as lithium hexamethyldisilazide or potassium hexamethyldisilazide in an inert solvent at a temperature of −78° C. to 100° C.

Step (2-4):

Method for producing compound (2-d): the compound (2-d) can be produced by performing "coupling reaction" using the carbonyl compound (2-c) and the compound (1-g).

Examples of the "coupling reaction" include the same coupling reactions as those previously described in Step (1-4).

The thus obtained compound (2-d) can be led to the compound [1] of the present invention by the method described in Steps (1-7) to (1-9) of the previously described Scheme 1.

Alternatively, the compound [1] of the present invention can also be produced by the following method.

Step (2-5):

Method for producing compound (2-e): the compound (2-e) possessing a protecting group $G^2$ can be produced by reacting di-tert-butyl dicarbonate or the like with the compound (2-d) containing a pyrrolidinyl group substituted with an oxo group.

Step (2-6):

Method for producing compound (2-f): the compound (2-f) can be produced by reducing the compound (2-e) as a matrix by a catalytic hydrogenation reaction with a catalytic amount of palladium-activated carbon, rhodium-activated carbon, platinum-activated carbon, or the like, in an inert solvent in the presence or absence of an acid at a temperature of 0° C. to 80° C.

Step (2-7):

Method for producing compound (2-g): the compound (2-g) can be produced by performing "deprotection reaction" of the protecting group $G^2$ possessed by the compound (2-f).

Examples of the deprotection reaction include a method using an acid such as hydrochloric acid or trifluoroacetic acid.

Step (2-8):

Method for producing compound [1] of the present invention: the compound [1] of the present invention can be produced by performing "deprotection reaction" of the protecting group $G^1$ possessed by the compound (2-g).

Examples of the "deprotection reaction" include the same deprotection reactions as those previously described in Step (1-8).

The compound (2-a) used as the raw material compound in the above Scheme 2 can be obtained as a commercial product or by a known method.

Finally, the crystal of 3-cyclopropyl-6-{(1R)-1-[4-(1,1-difluoroethyl)phenyl]-2-[(2R)-5-oxopyrrolidin-2-yl]ethyl}pyridin-2(1H)-one of the present invention and the method for producing the same are described.

The crystal of 3-cyclopropyl-6-{(1R)-1-[4-(1,1-difluoroethyl)phenyl]-2-[(2R)-5-oxopyrrolidin-2-yl]ethyl}pyridin-2(1H)-one of the present invention (hereinafter sometimes referred to as "crystal of the present invention") have the chemical structural formula represented by the above formula [1]. Further, the crystal of the present invention can be obtained in the form of single crystal having the consistent quality as described earlier with good reproducibility, can be supplied stably as the crystal of a drug substance used for producing pharmaceuticals, and has good storage stability.

The crystal of the present invention has physical properties of the following (a) to (c):

(a) an X-ray powder diffraction pattern (Cu—Kα, measurement method: transmission method) showing peaks at diffraction angles 2θ of 8.5, 10.8, 11.2, 11.6, 13.4, 16.8, 17.0, 17.9, 18.5, 18.8, 19.1, 19.4, 22.6, 23.1, 23.2 and 24.5°, particularly showing characteristic /peaks at diffraction angles 2θ of 8.5, 13.4, 19.1 and 24.5°;

(b) an infrared absorption spectrum (ATR method, crystal: diamond) showing characteristic absorption bands at 916, 1146, 1167, 1295, 1375, 1614, 1625, 1651, 1664, 2837, 2866, 2909, 2955, 2986, 3003, 3088 and 3146 cm$^{-1}$, particularly showing distinctive characteristic bands at 916, 1146, 1167, 1295, 1651, 1664, 2909, 2955, 3003 and 3146 cm$^{-1}$; and (c) a melting point of 199° C. to 201° C.

However, characteristic peaks by the X-ray powder diffraction may fluctuate depending on the measurement conditions. For this reason, peaks by the X-ray powder diffraction of the compounds of the present invention may sometimes have differences or may not be clear.

Figure 1:
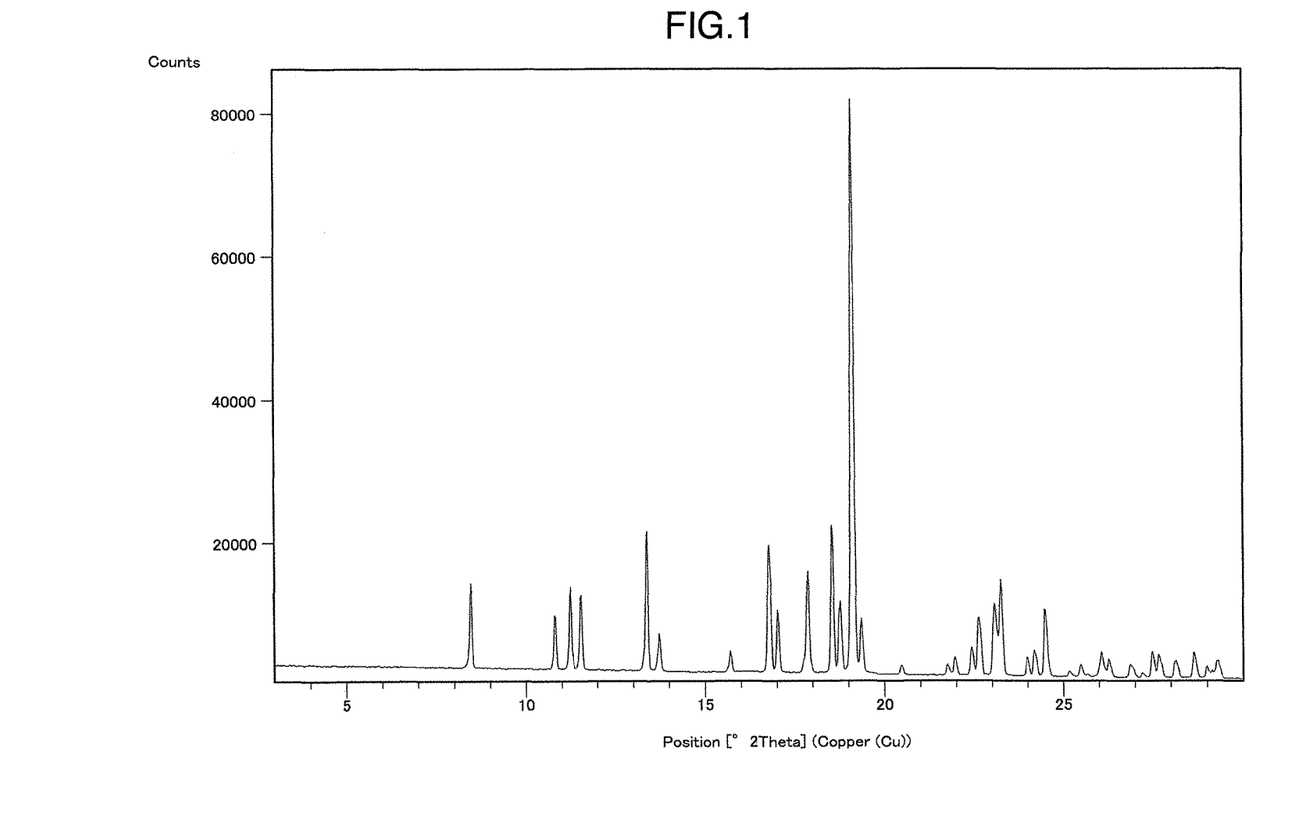
FIG. 1 is an X-ray powder diffraction pattern of the crystal of 3-cyclopropyl-6-{(1R)-1-[4-(1,1-difluoroethyl)phenyl]-2-[(2R)-5-oxopyrrolidin-2-yl]ethyl}pyridin-2(1H)-one of the present invention.
Figure 2:
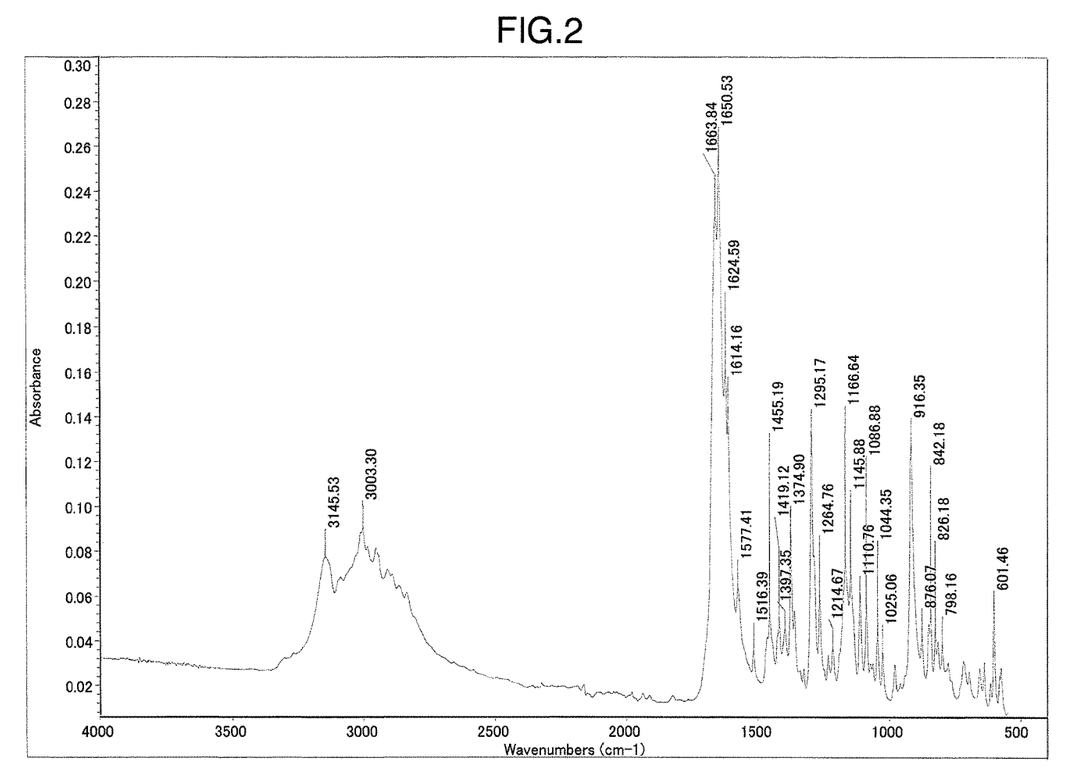
FIG. 2 is an infrared absorption spectrum (ATR method, crystal: diamond) of the crystal of 3-cyclopropyl-6-{(1R)-1-[4-(1,1-difluoroethyl)phenyl]-2-[(2R)-5-oxopyrrolidin-2-yl]ethyl}pyridin-2(1H)-one of the present invention.
Figure 3:
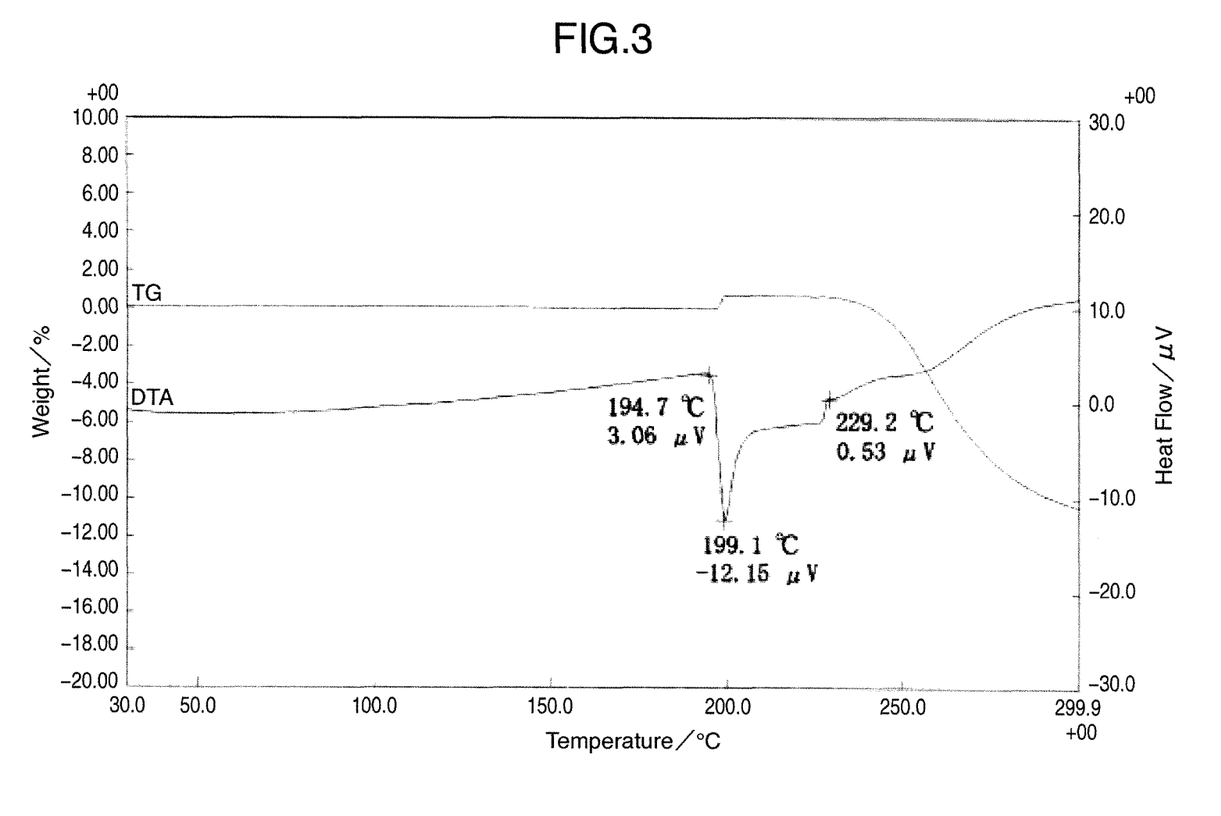
FIG. 3 shows differential thermal analysis/thermogravimetric curves of the crystal of 3-cyclopropyl-6-{(1R)-1-[4-(1,1-difluoroethyl)phenyl]-2-[(2R)-5-oxopyrrolidin-2-yl]ethyl}pyridin-2(1H)-one of the present invention.

The crystal of the present invention has the X-ray powder diffraction pattern as shown in FIG. 1, the infrared absorption spectrum (ATR method, crystal: diamond) as shown in FIG. 2, and the differential thermal analysis/thermogravimetric curves as shown in FIG. 3.

The crystal of the present invention can be produced by crystallizing 3-cyclopropyl-6-{(1R)-1-[4-(1,1-difluoroethyl)phenyl]-2-[(2R)-5-oxopyrrolidin-2-yl]ethyl}pyridin-2(1H)-one using an alcohol solvent.

The 3-cyclopropyl-6-{(1R)-1-[4-(1,1-difluoroethyl)phenyl]-2-[(2R)-5-oxopyrrolidin-2-yl]ethyl}pyridin-2(1H)-one as a raw material is an amorphous or a crystal before being dissolved in an alcohol solvent.

When the crystal of the present invention is obtained by the crystallization or recrystallization using an alcohol solvent, the dissolution of 3-cyclopropyl-6-{(1R)-1-[4-(1,1-difluoroethyl)phenyl]-2-[(2R)-5-oxopyrrolidin-2-yl]ethyl}pyridin-2(1H)-one into an alcohol solvent and the crystallization of it from the alcohol solution can be carried out by the conventional manner. For example, a method in which an amorphous 3-cyclopropyl-6-{(1R)-1-[4-(1,1-difluoroethyl)phenyl]-2-[(2R)-5-oxopyrrolidin-2-yl]ethyl}pyridin-2(1H)-one is dissolved in an alcohol solvent while heating and subsequently cooled is employed.

Examples of the solvent compatible with an alcohol solvent include a water solvent and hydrocarbon solvents such as heptane.

The mixing ratio of an alcohol solvent to a solvent compatible with the alcohol solvent in the mixed solvent can be suitably changed.

The alcohol solvent used is preferably alcohol having 1 to 4 carbon atoms such as methanol, ethanol, 1-propanol, isopropyl alcohol, tert-butyl alcohol, 1-butanol, 2-butanol, 2-ethoxy ethanol, 2-methoxy ethanol, trifluoroethanol, ethylene glycol, and propylene glycol; more preferably methanol, ethanol, isopropyl alcohol or propylene glycol; and still more preferably methanol or ethanol.

The concentration of the dissolved 3-cyclopropyl-6-{(1R)-1-[4-(1,1-difluoroethyl)phenyl]-2-[(2R)-5-oxopyrrolidin-2-yl]ethyl}pyridin-2(1H)-one is 1 to 50% by mass, preferably 17 to 25% by mass. The % by mass used herein refers to the percent by mass of the 3-cyclopropyl-6-{(1R)-1-[4-(1,1-difluoroethyl)phenyl]-2-[(2R)-5-oxopyrrolidin-2-yl]ethyl}pyridin-2(1H)-one in the solution.

The crystallization of 3-cyclopropyl-6-{(1R)-1-[4-(1,1-difluoroethyl)phenyl]-2-[(2R)-5-oxopyrrolidin-2-yl]ethyl}pyridin-2(1H)-one can be carried out at a temperature from −78° C. to the reflux temperature of a solvent, but a preferable example is a method comprising dissolving 3-cyclopropyl-6-{(1R)-1-[4-(1,1-difluoroethyl)phenyl]-2-[(2R)-5-oxopyrrolidin-2-yl]ethyl}pyridin-2(1H)-one in an alcohol solvent while heating the solution to 55° C. to 75° C.; subsequently, in some cases, adding a solvent compatible with the alcohol solvent such as water to the solution; and cooling down the solution to 5° C. or lower to allow the crystal to precipitate.

The cooling time is not particularly limited as long as it is 10 seconds or longer, but is typically 10 minutes to 24 hours, preferably 30 minutes to 5 hours. From the viewpoint of industrial production, it is preferably 2 hours to 4 hours.

The precipitated crystal is separated from the solution by filtering or centrifuging the suspension, which is subsequently dried at 60° C. or lower.

Further, a seed crystal can be used for the crystallization. The seed crystal can be prepared beforehand by a method well known to a person skilled in the art, such as scraping the wall of a container carrying a solution for crystal precipitation using a spatula.

The reaction temperature in the general processes for producing the compounds of the present invention is −78° C. to 250° C., and preferably −20° C. to 80° C. The reaction time is 5 minutes to 3 days, and preferably 30 minutes to 18 hours. The production processes may be performed under normal pressure, under pressure or under microwave irradiation, for example.

The base, the acid and the inert solvent in the description of the general processes for producing the compounds of the present invention will be more specifically described, but are not limited to the following illustrations. The usable isolation techniques will also be specifically described, but are similarly not limited to the following illustrations.

Examples of the "base" include inorganic bases such as alkali metal or alkaline earth metal hydrides (such as lithium hydride, sodium hydride, potassium hydride and calcium hydride), alkali metal or alkaline earth metal amides (such as lithium amide, sodium amide, lithium diisopropylamide, lithium dicyclohexylamide, lithium hexamethyldisilazide and potassium hexamethyldisilazide), alkali metal or alkaline earth metal $C_1$-$C_6$ alkoxides (such as sodium methoxide, sodium ethoxide and potassium tert-butoxide), alkali metal or alkaline earth metal hydroxides (such as sodium hydroxide, potassium hydroxide, lithium hydroxide and barium hydroxide), alkali metal or alkaline earth metal carbonates (such as sodium carbonate, potassium carbonate, calcium carbonate and cesium carbonate), alkali metal bicarbonates (such as sodium bicarbonate and potassium bicarbonate) and alkali metal or alkaline earth metal phosphates (such as tripotassium phosphate), amines (such as triethylamine, diisopropylethylamine and N-methylmorpholine) and basic heterocyclic compounds (such as pyridine, 4-dimethylaminopyridine, DBU (1,8-diazabicyclo[5.4.0]undec-7-ene), DBN (1,5-diazabicyclo[4.3.0]nonane-5-ene), imidazole and 2,6-lutidine).

Examples of the "acid" include inorganic acids (such as hydrochloric acid, hydrobromic acid, sulfuric acid, nitric acid and phosphoric acid), organic acids (such as p-toluenesulfonic acid, methanesulfonic acid, trifluoroacetic acid, formic acid, acetic acid and camphorsulfonic acid) and Lewis acids (such as boron trifluoride, boron tribromide, aluminum chloride, scandium triflate and ytterbium triflate).

The "inert solvent" is not limited as long as it does not inhibit the reaction and dissolves the starting material to some extent, and the examples thereof include nitrile solvents, amide solvents, halocarbon solvents, ether solvents, aromatic solvents, hydrocarbon solvents, ester solvents, alcohol solvents, sulfoxide solvents and water. These solvents may be used as a mixture of two or more solvents in an appropriate proportion.

Examples of the nitrile solvents include acetonitrile and propionitrile. Examples of the amide solvents include N,N-dimethylformamide (hereinafter sometimes abbreviated as DMF), N,N-dimethylacetamide and N-methylpyrrolidone. Examples of the halocarbon solvents include dichloromethane, chloroform, 1,2-dichloroethane and carbon tetrachloride. Examples of the ether solvents include diethyl ether (hereinafter sometimes abbreviated as "ether"), tetrahydrofuran (hereinafter sometimes abbreviated as THF), 1,4-dioxane and 1,2-dimethoxyethane. Examples of the aromatic solvents include benzene, toluene, xylene and pyridine. Examples of the hydrocarbon solvents include hexane, pentane and cyclohexane. Examples of the ester solvents include ethyl acetate and ethyl formate. Examples of the alcohol solvents include methanol, ethanol, isopropyl alcohol, tert-butyl alcohol and ethylene glycol. Examples of the sulfoxide solvents include dimethyl sulfoxide (hereinafter sometimes abbreviated as DMSO).

Compounds obtained by the above production processes can be isolated and purified by known means such as solvent extraction, liquidity change, transfer, crystallization, recrystallization and various kinds of chromatography techniques.

Protecting groups that can be used by the compounds in the general processes for producing the compounds of the present invention will be described below, but are not limited to such illustrations; other protecting groups may also be suitably selected.

Examples of the protecting group $G^2$ include $C_1$-$C_6$ acyl groups (such as formyl, acetyl and propionyl), $C_2$-$C_{15}$ alkoxycarbonyl groups (such as methoxycarbonyl, ethoxycarbonyl, tert-butoxycarbonyl, benzyloxycarbonyl and 9-fluorenylmethyleneoxycarbonyl), arylcarbonyl groups (such as benzoyl), a trityl group, a phthaloyl group, a N,N-dimethylaminomethylene group, substituted silyl groups (such as trimethylsilyl, triethylsilyl, dimethylphenylsilyl, tert-butyldimethylsilyl and tert-butyldiethylsilyl) and $C_2$-$C_6$ alkenyl groups (such as 1-allyl), each of which is generally used in peptide synthesis. These groups may be substituted with one or more substituents selected from halogen atoms, $C_1$-$C_6$ alkoxy groups (such as methoxy, ethoxy and propoxy) and a nitro group.

EXAMPLES

The present invention will be described in more detail by the following Examples and Test Examples. These examples do not limit the present invention and may be changed within the scope of the present invention.

In the following Examples, NH silica gel column chromatography refers to a column chromatography separation and purification using an NH2 type silica gel (Chromatorex (registered trademark) NH2 type, Biotage (registered trademark) SNAP KP-NH Catridge). The elution solvent ratio is expressed by the volume ratio unless indicated otherwise.

For silica gel column chromatography, Kanto Chemical Co. "Silica Gel 60", Fuji Silysia "PSQ60B" or a packed column (YAMAZEN HiFlash™ Column, MORITEX Purif Pack or Biotage (registered trademark) SNAP KP-Sil Catridge) was used.

The abbreviations used in the present specification mean as follows.
s: singlet
d: doublet
t: triplet
q: quartet
dd: double doublet
m: multiplet
br: broad
J: coupling constant
Hz: Hertz
$CDCl_3$: Chloroform-d $^1$H-NMR (proton nuclear magnetic resonance spectrum) was measured using the following Fourier transform NMRs.
300 MHz: JNM-ECP300 (JEOL), JNM-ECX300 (JEOL)
600 MHz: JNM-ECA600 (JEOL)

ACD/SpecManager ver.12.01 (tradename), or the like, was used for the analysis.

MS (mass spectrum) was measured using the following apparatuses. micromass ZQ (Waters)
LTQ XL (Thermo Fisher Scientific)
LCMS-2010EV (Shimadzu)
LCMS-IT-TOF (Shimadzu)
Agilent 6150 (Agilent)
LCQ Deca XP (Thermo Fisher Scientific)

For the ionization method, an ESI (Electrospray Ionization) method or a dual ionization method of ESI and APCI (Atmospheric Pressure Chemical Ionization) was used.

The optical rotation measurement was carried out using a JASCO Corporation polarimeter (Model No.: P-1020).

The X-ray powder diffraction measurement was carried out using a PANalytical X'Pert PRO MPD (source of radiation: Cu.Kα).

The infrared absorption spectrum measurement was carried out by the ATR method (attenuated total reflection) using a Thermo Fisher Scientific Nicolet iS5.

The melting point measurement was carried out using a Mettler Toledo MP90 automatic melting point determination system.

For the preparative HPLC column, Daicel Chemical Industries, LTD. CHIRALPAK IB 5 μm (I. D. 20 mm, Length 250 mm), or the like, was used.

For the analytical HPLC column, Daicel Chemical Industries, LTD. CHIRALPAK IB 5 μm (I. D. 4.6 mm, Length 250 mm), or the like, was used.

The nomenclature for chemical compounds was based on ACD/Name ver.12.01 (tradename), or the like.

Example 1

3-Cyclopropyl-6-{(1R)-1-[4-(1,1-difluoroethyl)phenyl]-2-[(2R)-5-oxopyrrolidin-2-yl]ethyl}pyridin-2(1H)-one

[Formula 5]

(1) 1-Bromo-4-(1,1-difluoroethyl)benzene

[Formula 6]

Deoxo-Fluor (registered trademark) (22.2 g) was added to 1-(4-bromophenyl)ethanone (20.0 g) and the mixture was stirred at 85° C. for 15 hours. Under ice-cooling, ice water and an aqueous solution of potassium carbonate were added to the reaction solution, followed by extraction with chloroform. The solvent was evaporated under reduced pressure and the obtained residue was purified by silica gel column chromatography (hexane) to give the title compound (13.0 g, yield 59%) as a yellow oil.

$^1$H NMR (600 MHz, CDCl$_3$) δ ppm 1.91 (t, J=18.2 Hz, 3H), 7.50 (d, J=8.3 Hz, 2H), 7.86 (d, J=8.3 Hz, 2H).

(2) 2-[4-(1,1-Difluoroethyl)phenyl]-4,4,5,5-tetramethyl-1,3,2-dioxaborolane

[Formula 7]

Bispinacol diborate (22.5 g), [1,1'-bis(diphenylphosphino)ferrocene]palladium(II) dichloride-dichloromethane complex (904 mg) and potassium acetate (8.70 g) were added to a solution of 1-bromo-4-(1,1-difluoroethyl)benzene (9.80 g) synthesized in Example 1-(1) in 1,4-dioxane (60 mL), and stirred at 90° C. for 10 hours. The reaction solution was poured into water, followed by extraction with chloroform. The solvent was evaporated under reduced pressure and the obtained residue was purified by silica gel column chromatography (hexane) to give the title compound (7.87 g, yield 66%) as a colorless solid.

$^1$H NMR (600 MHz, CDCl$_3$) δ ppm 1.35 (s, 12H), 1.91 (t, J=18.2 Hz, 3H), 7.50 (d, J=7.8 Hz, 2H), 7.86 (d, J=7.8 Hz, 2H).

(3) 5-Cyclopropyl-6-methoxypyridin-2-carbaldehyde

[Formula 8]

A 2M solution of n-butylmagnesium chloride in tetrahydrofuran (74.5 mL) was added to a mixed solvent of toluene (433 mL)-tetrahydrofuran (116 mL) in an argon atmosphere. A 1.6M solution of n-butyllithium in tetrahydrofuran (186 mL) was added dropwise at −12° C., stirred for 40 minutes, and subsequently 6-bromo-3-cyclopropyl-2-methoxypyridine (34.0 g) was added thereto. After stirring further 1 hour, N,N-dimethylformamide (32.7 g) was added dropwise thereto. After further stirring for 1 and a half hours, the reaction solution was added to a 13% aqueous solution of citric acid and extracted, and subsequently the organic layer was washed with water. The solvent was evaporated under reduced pressure and the obtained residue was purified by silica gel column chromatography (hexane:ethyl acetate=95:5 90:10) to give the title compound (21.2 g, yield 80%) as a yellow oil.

$^1$H NMR (600 MHz, CDCl$_3$) δ ppm 0.73-0.78 (m, 2H), 1.03-1.08 (m, 2H), 2.14-2.21 (m, 1H), 4.07 (s, 3H), 7.19 (d, J=7.4 Hz, 1H), 7.49 (d, J=7.4 Hz, 1H), 9.92 (s, 1H).

MS (+): 178[M+H]$^+$.

(4), (5) (5R)-5-[(Z)-2-Bromo-2-(5-cyclopropyl-6-methoxypyridin-2-yl)ethenyl]pyrrolidin-2-one

[Formula 9]

(4) A 1M solution of potassium hexamethyldisilazide in tetrahydrofuran (405 mL) was added dropwise at −78° C. to a solution of (5R)-5-[(1,3-benzothiazol-2-ylsulfonyl) methyl]pyrrolidin-2-one (30.0 g) and lithium chloride (8.58 g) in tetrahydrofuran (1.2 L), and subsequently stirred for 1 hour. A solution of 5-cyclopropyl-6-methoxypyridine-2-carbaldehyde (17.9 g) synthesized in Example 1-(3) in tetrahydrofuran (600 mL) was added dropwise thereto and further stirred for 0.5 hour. A saturated ammonium chloride solution (500 mL) was added to the reaction solution, followed by extraction with ethyl acetate. The organic layer was washed with brine, dried over magnesium sulfate, followed by separating the desiccant by filtration, and evaporating the solvent under reduced pressure. The obtained residue was purified twice by silica gel column chromatography (hexane:ethyl acetate=100:0→70:30) to obtain (5R)-5-[(Z)-2-(5-cyclopropyl-6-methoxypyridin-2-yl)ethenyl]pyrrolidin-2-one (8.40 g, yield 34%) as a yellow oil.

$^1$NMR (600 MHz, CDCl$_3$) δ ppm 0.62-0.68 (m, 2H), 0.93-0.99 (m, 2H), 1.89-1.97 (m, 1H), 2.03-2.09 (m, 1H), 2.33-2.56 (m, 3H), 3.98 (s, 3H), 5.53-5.55 (m, 1H), 5.70 (dd, J=11.56, 7.84 Hz, 1H), 5.94-6.03 (br.s., 1H), 6.34 (dd, J=11.56, 1.24 Hz, 1H), 6.70 (d, J=7.43 Hz, 1H), 7.07 (d, J=7.43 Hz, 1H).

MS (+): 259[M+H]$^+$.

(5) Bromine (1.33 mL) was added dropwise to a solution of (5R)-5-[(Z)-2-(5-cyclopropyl-6-methoxypyridin-2-yl) ethenyl]pyrrolidin-2-one (8.40 g) synthesized in Example 1-(4) in chloroform (126 mL) at 0° C. After stirring for 1 hour, a solution of 1,8-diazabicyclo[5.4.0]undec-7-ene (9.7 mL) in chloroform (42 mL) was added dropwise over a period of 30 minutes and stirred for 15 minutes. One M hydrochloric acid (200 mL) was added to the reaction solution, followed by extraction with ethyl acetate. The organic layer was washed with brine, dried over magnesium sulfate, followed by separating the desiccant by filtration, and evaporating the solvent under reduced pressure. The obtained residue was purified by silica gel column chromatography (hexane:ethyl acetate=50:50→0:100) to give the title compound (7.50 g, yield 68%) as a yellow solid.

$^1$H NMR (600 MHz, CDCl$_3$) δ ppm 0.65-0.68 (m, 2H), 0.95-1.00 (m, 2H), 1.96-2.10 (m, 2H), 2.40-2.59 (m, 3H), 4.00 (s, 3H), 4.80 (q, J=7.4 Hz, 1H), 5.68-5.70 (br.s., 1H), 7.10 (d, J=7.8 Hz, 1H), 7.15 (d, J=7.8 Hz, 1H), 7.24 (d, J=7.8 Hz, 1H).

MS (+): 337[M+H]$^+$.

(6) (5R)-5-{(E)-2-(5-Cyclopropyl-6-methoxypyridin-2-yl)-2-[4-(1,1-difluoroethyl)phenyl]ethenyl}pyrrolidin-2-one

[Formula 10]

In a nitrogen atmosphere, 2-[4-(1,1-difluoroethyl)phenyl]-4,4,5,5-tetramethyl-1,3,2-dioxaborolane (1.59 g) synthesized in Example 1-(2), cesium carbonate (1.92 g), tris (dibenzylideneacetone)dipalladium (0) (271 mg), tri(2-furyl)phosphine (412 mg) and distilled water (10 mL) were added to a solution of (5R)-5-[(Z)-2-bromo-2-(5-cyclopropyl-6-methoxypyridin-2-yl)ethenyl]pyrrolidin-2-one (1.0 g) synthesized in Example 1-(5) in 1,4-dioxane (50 mL), and the mixture was stirred at 90° C. for 2 hours. The reaction solution was poured into water, followed by extraction with ethyl acetate. The organic layer was dried over anhydrous magnesium sulfate, followed by separating the desiccant by filtration, and evaporating the solvent under reduced pressure. The obtained residue was purified by silica gel column chromatography (hexane:ethyl acetate=100:0→0:100), further by NH silica gel column chromatography (hexane:ethyl acetate=100:0→0:100) to give the title compound (1.13 g, yield 96%) as a colorless amorphous.

$^1$H NMR (600 MHz, CDCl$_3$) δ ppm 0.56-0.64 (m, 2H), 0.90-0.97 (m, 2H), 1.93-2.09 (m, 5H), 2.20-2.34 (m, 2H), 2.37-2.45 (m, 1H), 4.04 (s, 3H), 4.07-4.16 (m, 1H), 5.73-5.75 (br.s., 1H), 6.23 (d, J=7.4 Hz, 1H), 6.90 (d, J=9.9 Hz, 1H), 6.92 (d, J=7.8 Hz, 1H), 7.24 (d, J=8.3 Hz, 2H), 7.57 (d, J=7.8 Hz, 2H).

MS (+): 399[M+H]$^+$.

(7) (5R)-5-{2-(5-Cyclopropyl-6-methoxypyridin-2-yl)-2-[4-(1,1-difluoroethyl)phenyl]ethyl}pyrrolidin-2-one

[Formula 11]

In a nitrogen atmosphere, 10% palladium-activated carbon (110 mg) was added to a solution of (5R)-5-{(E)-2-(5-cyclopropyl-6-methoxypyridin-2-yl)-2-[4-(1,1-difluoroethyl) phenyl]ethenyl}pyrrolidin-2-one (1.1 g) synthesized in Example 1-(6) in methanol (44 mL) and the mixture was stirred at room temperature for 1 hour in a hydrogen atmosphere. After filtering the reaction solution using Celite (registered trademark), the solvent was evaporated under reduced pressure to give the title compound (1.10 g, yield 99%) as a colorless amorphous.

MS(±): 401[M+H]$^+$.

(8) 3-Cyclopropyl-6-{1-[4-(1,1-difluoroethyl)phenyl]-2-[(2R)-5-oxopyrrolidin-2-yl]ethyl}pyridin-2(1H)-one

[Formula 12]

Chlorotrimethylsilane (707 μL) and potassium iodide (1.37 g) were added to a solution of (5R)-5-{2-(5-cyclopropyl-6-methoxypyridin-2-yl)-2-[4-(1,1-difluoroethyl)phenyl]ethyl}pyrrolidin-2-one (1.1 g) synthesized in Example 1-(7) in acetonitrile (30 mL) and the mixture was stirred at 60° C. for 1 hour. The reaction solution was poured into water, followed by extraction with ethyl acetate. The organic layer was washed with brine, dried over anhydrous magnesium sulfate, followed by separating the desiccant by filtration and evaporating the solvent under reduced pressure. The obtained residue was purified by silica gel column chromatography (chloroform:methanol=100:0→80:20) to give the title compound (880 mg, yield 83%) as a colorless amorphous.

MS(+):387[M+H]$^+$.

(9) 3-Cyclopropyl-6-{(1R)-1-[4-(1,1-difluoroethyl)phenyl]-2-[(2R)-5-oxopyrrolidin-2-yl]ethyl}pyridin-2(1H)-one

[Formula 13]

ARS mixture (180 mg) of 3-cyclopropyl-6-{1-[4-(1,1-difluoroethyl)phenyl]-2-[(2R)-5-oxopyrrolidin-2-yl]ethyl}pyridin-2(1H)-one synthesized in Example 1-(8) was fractionated using a chiral HPLC column (CHIRALPAK IB, hexane:ethanol=70:30 v/v, 40° C., 12 mL/min, 254 nm) to give the title compound (70 mg) as a colorless amorphous and the diastereomer (67 mg) of the title compound as a colorless amorphous.

$^1$H NMR (600 MHz, CDCl$_3$) δ ppm 0.54-0.67 (m, 2H), 0.90-0.98 (m, 2H), 1.68-1.75 (m, 1H), 1.88 (t, J=18.2 Hz, 3H), 2.07-2.14 (m, 1H), 2.14-2.40 (m, 5H), 3.43-3.52 (m, 1H), 4.07-4.12 (m, 1H), 6.00 (d, J=7.0 Hz, 1H), 6.92 (d, J=7.0 Hz, 1H), 7.41-7.47 (m, 4H), 7.60-7.68 (m, 1H), 12.28-12.49 (br.s., 1H).

MS (+): 387[M+H]$^+$.

CHIRALPAK IB 4.6×250 mm 5 μm (DAICEL), hexane:ethanol=70:30 v/v, 40° C., 1.0 mL/min, 210 nm, Rt=7.5 min.

Diastereomer

[Formula 14]

$^1$H NMR (600 MHz, CDCl$_3$) δ ppm 0.54-0.66 (m, 2H), 0.95-1.05 (m, 2H), 1.75-1.84 (m, 1H), 1.90 (t, J=18.0 Hz, 3H), 2.15-2.41 (m, 6H), 3.54-3.64 (m, 1H), 4.16 (dd, J=10.1, 5.57 Hz, 1H), 6.01 (s, 1H), 6.96 (d, J=7.0 Hz, 1H), 7.39 (d, J=8.26 Hz, 2H), 7.47 (s, 2H), 7.83-7.92 (m, 1H), 13.14-13.34 (br.s., 1H).

MS (+): 387[M+H]$^+$.

CHIRALPAK IB 4.6×250 mm 5 μm (DAICEL), hexane:ethanol=70:30 v/v, 40° C., 1.0 mL/min, 210 nm, Rt=18.9 min.

Example 2

(5R)-5-{2-(5-Cyclopropyl-6-methoxypyridin-2-yl)-2-[4-(1,1-difluoroethyl)phenyl]ethenyl}pyrrolidin-2-one

[Formula 15]

(1) (5-Cyclopropyl-6-methoxypyridin-2-yl)[4-(1,1-difluoroethyl)phenyl]methanone

[Formula 16]

In a nitrogen atmosphere, a 1.6 M solution of n-butyllithium in tetrahydrofuran (127 mL) was added dropwise to a solution of 6-bromo-3-cyclopropyl-2-methoxypyridine (41.5 g) in tetrahydrofuran (273 mL) at −78° C. over a period of 50 minutes, followed by stirring at −78° C. for 1 hour. Subsequently, a solution of 4-(1,1-difluoroethyl)benzonitrile (24.3 g) in tetrahydrofuran (137 mL) was added dropwise to the reaction solution while maintaining the temperature at −78° C. over a period of 75 minutes, further followed by stirring for 1 hour. After the temperature of the reaction solution was raised to 0° C., 1M hydrochloric acid (437 mL), tetrahydrofuran (365 mL) and 1M hydrochloric acid (146 mL) were sequentially added dropwise thereto.

The reaction solution was separated into the organic layer and the aqueous layer, followed by extracting the aqueous layer with ethyl acetate (1000 mL). The combined organic layers were dried over anhydrous magnesium sulfate, the desiccant was separated by filtration, and subsequently the solvent was evaporated under reduced pressure. The obtained residue was purified by silica gel column chromatography (hexane:ethyl acetate=100:0→95:5) to give the title compound (34.0 g, yield 74%) as a colorless oil.

$^1$H NMR (300 MHz, CDCl$_3$) δ ppm 0.72-0.81 (m, 2H), 1.00-1.10 (m, 2H), 1.96 (t, J=18.2 Hz, 3H), 2.10-2.25 (m, 1H), 3.95 (s, 3H), 7.24 (d, J=6.9 Hz, 1H), 7.59 (d, J=9.0 Hz, 2H), 7.67 (d, J=7.8 Hz, 1H), 8.21 (d, J=8.6 Hz, 2H).

MS (+): 318[M+H]$^+$.

(2) (5R)-5-{2-(5-Cyclopropyl-6-methoxypyridin-2-yl)-2-[4-(1,1-difluoroethyl)phenyl]ethenyl}pyrrolidin-2-one

[Formula 17]

In a nitrogen atmosphere, a 1.0 M solution of lithium hexamethyldisilazide in tetrahydrofuran (317 mL) was added dropwise to a solution of (5-cyclopropyl-6-methoxypyridin-2-yl)[4-(1,1-difluoroethyl)phenyl]methanone (33.5 g) obtained in Example 2-(1) and (5R)-5-[(1,3-benzothiazol-2-ylsulfonyl)methyl]pyrrolidin-2-one (37.5 g) in dichloromethane (1007 mL) over a period of 50 minutes at −78° C. and the mixture was stirred at −78° C. for 4 hours and 40 minutes.

After the temperature of the reaction solution was raised to 0° C., a saturated aqueous ammonium chloride solution (335 g) was added dropwise to complete the reaction. The reaction solution was separated into an organic layer and an aqueous layer, followed by extracting the aqueous layer with chloroform (339 mL) and washing the combined organic layers with water (502 g). The organic layer was dried over anhydrous magnesium sulfate, the desiccant was separated by filtration, and subsequently the solvent was evaporated under reduced pressure. The obtained residue was purified by silica gel column chromatography (hexane:ethyl acetate=50:50→0:100) to give the title compound which was a E/Z mixture as a light yellow amorphous (42.7 g, E:Z=50:50).

The mixing ratio was determined by the area percentage of liquid chromatography.

The conditions for liquid chromatography were as follows.

L-Column ODS, CH$_3$CN:0.01 M acetate buffer (0.01 M aqueous acetic acid solution: 0.01 M aqueous sodium acetate solution=8:1)=80:20 v/v, 1.0 mL/min, 40° C., 254 nm, E: Rt=5.40 min, Z:Rt=5.08 min.

MS(+) :399[M+H]$^+$.

Hereinafter, the title compound can be proceeded to the compound [1] by the methods described in Examples 1 (7) to (9) or a method in accordance therewith.

Example 3

Crystal of compound [1]
Method for Crystallizing Compound [1]

Water (29 g) was added dropwise to a solution of 3-cyclopropyl-6-{(1R)-1-[4-(1,1-difluoroethyl)phenyl]-2-[(2R)-5-oxopyrrolidin-2-yl]ethyl}pyridin-2(1H)-one (14.4 g) in ethanol (72 g) at 75° C. While gradually cooling down from 75° C., a piece of seed crystal was added at the time of reaching an inner temperature of 40° C. and the temperature was cooled to room temperature. The temperature was further cooled to 0° C., and the solution was stirred overnight to prepare a suspension.

The temperature was returned to room temperature, the obtained solid was collected by filtration, washed with water and dried (50° C., 6 hours) to give 8.7 g (yield 60%) of a colorless crystal.

(a) An X-ray powder diffraction pattern (Cu—Kα, measurement method: transmission method) shows peaks at diffraction angles 2θ of 8.5, 10.8, 11.2, 11.6, 13.4, 16.8, 17.0, 17.9, 18.5, 18.8, 19.1, 19.4, 22.6, 23.1, 23.2 and 24.5°.
(b) An infrared absorption spectrum (ATR method, crystal: diamond) shows characteristic absorption bands at 916, 1146, 1167, 1295, 1375, 1614, 1625, 1651, 1664, 2837, 2866, 2909, 2955, 2986, 3003, 3088 and 3146 cm$^{-1}$.
(c) A melting point is 199° C. to 201° C.
(d) A specific optical rotation is [α]$_D^{23}$=+36 (c0.1, MeOH).

The GK activating effect of the compounds of the present invention can be evaluated in accordance with a known technique such as the method described in Test Examples.

The GK activating effects of the compound [1] of the present invention, the compound A (Example 4-302), the compound B (Example 4-248) and the compound C (Example 4-340) disclosed in WO 2011/068211 were measured using the method described in the following Test Examples.

The structures of the compound A, the compound B and the compound C disclosed in WO 2011/068211 are shown below.

[Formula 18]

Compound A

Compound B

Compound C (Test Example 1.)

GK Activation Test

The GK activation test for the test compounds was carried out by the method of Van Schaftingen et al. (Eur. J. Biochem. 179:179-184, 1989) with partial modifications. The GK activity was measured by the change in the absorbance based on an amount of thio-NADH, which is a reduced form product converted from thio-NAD+ (thionicothinamide-adeninedinucleotide) when dehydrogenating glucose 6-phosphate, produced by GK using glucose as a matrix, with G6PDH (glucose-6-phosphate dehydrogenase).

The enzyme source used in this assay, human liver GK, was expressed in *E. coli* as a fusion protein with GST (glutathione S-transferase) added to the amino terminus and was purified using Glutathione Sepharose 4B (Amersham Biosciences).

The test was carried out using flat-bottom 96-well half area microplates (Corning). A solution of the test compound in dimethyl sulfoxide (DMSO) at a final concentration of 1% in DMSO and DMSO as a control were added to each well of the plates. Further, 25 mM Hepes-KOH (pH=7.1), 25 mM KCl, 2 mM $MgCl_2$, 2 mM thio-NAD+, 4 mM glucose, 1 mM DTT (dithiothreitol), 0.01 units/µL G6PDH and 2 µg/mL human liver GK were added as the final concentrations, respectively, to each of the wells. Subsequently, ATP was added to each of the wells to give the final concentration of 2 mM, and the reaction was started. The microplates were allowed to stand at room temperature. After 15 minutes from the start of reaction, the absorbance at 405 nm was measured using an absorption spectrometer for microplate.

The GK activity maximally activated by the test compound was taken as the maximum activation ability, and the test compound concentration (nM) needed to activate 50% of that maximum activation ability was expressed as $EC_{50}$.

The results are shown below.

TABLE 1

| Compound | $EC_{50}$ [nM] |
| --- | --- |
| Compound [1] | 295 |
| Compound A | 520 |
| Compound B | 1326 |
| Compound C | 597 |

(Test Example 2.)

Hypoglycemia Test using C57BL6/J Mice

The test to verify the hypoglycemic effect of the test compounds was carried out in accordance with a method commonly used and represented by the method of Grimsby et. al (Science 301: 370-373, 2003).

The body weight of C57BL6/J mice (N=6), who were ad libitum fed before the test, was measured. The test compound was suspended or dissolved in the base to be administered (0.5% methyl cellulose) at a concentration of 0.06 to 20 mg/mL. The mice were orally administered with 5 mL/kg of a drug solution (equivalent to 0.3 to 100 mg/kg of the test compound) or control (only the base to be administered). About 60 µL of blood was collected from the tail vein using a capillary tube immediately before administration of the test compound and 0.5, 1, 2, 4 and 6 hours after administration of the test compound. The collected blood was centrifuged and subsequently measured for the plasma glucose concentration. The area under the curve (AUC) was calculated from changes over time in the plasma glucose concentration after administration of the test compound, and a reduction rate (%) to AUC of the control group was calculated. The dose at which an AUC decreasing percentage was 20% ($ED_{20}$ value; mg/kg) was calculated from the dose response curve having the AUC reduction rate plotted on the vertical axis and the dose plotted on the horizontal axis.

The results are shown below.

TABLE 2

| Compound | $ED_{20}$ [mg/kg] |
| --- | --- |
| Compound [1] | 4.2 |
| Compound A | 11.5 |

TABLE 2-continued

| Compound | $ED_{20}$ [mg/kg] |
| --- | --- |
| Compound B | 15.6 |
| Compound C | 32.0 |

The above test results ascertained that the compounds of the present invention show good hypoglycemic effects from a low dose range. In conclusion, the compounds of the present invention are useful as a prophylactic/therapeutic agent for diabetes, and the like, and the therapeutic range thereof is evidently wider than other compounds.

Further, the compounds of the present invention, when compared with three compounds disclosed in WO 2011/068211, were revealed to have a much stronger hypoglycemic effect.

Additionally, the compounds of the present invention have properties desirable to be pharmaceuticals. Examples of such a property include good hypoglycemic effects by exhibiting good physical properties and pharmacokinetics (e.g., hepatic metabolism stability).

INDUSTRIAL APPLICABILITY

The compounds of the present invention have an excellent GK activating effect and can provide therapeutic and prophylactic agents not only for diabetes but also for diabetes-related diseases such as obesity and hyperlipidemia or chronic diabetic complications such as retinopathy, nephropathy and arteriosclerosis.

The invention claimed is:
1. A compound represented by formula [1]:

[1]

a tautomer of the compound, a pharmaceutically acceptable salt thereof, or a solvate of the compound, the tautomer thereof, or the salt thereof.

2. The compound according to claim 1, which is a crystal of 3-cyclopropyl-6-{(1R)-1-[4-(1,1-difluoroethyl)phenyl]-2-[(2R)-5-oxopyrrolidin-2-yl]ethyl}pyridin-2(1H)-onehaving
an X-ray powder diffraction pattern (Cu—Kα) showing peaks at diffraction angles 2θ of 8.5, 13.4, 19.1 and 24.5°.

3. The compound according to claim 1, which is a crystal of 3-cyclopropyl-6-{(1R)-1-[4-(1,1-difluoroethyl)phenyl]-2-[(2R)-5-oxopyrrolidin-2-yl]ethyl}pyridin-2(1H)-one having physical properties of the following (a) to (c):
(a) an X-ray powder diffraction pattern (Cu—Kα) showing peaks at diffraction angles 2θ of 8.5, 13.4, 19.1 and 24.5°;
(b) an infrared absorption spectrum showing characteristic absorption bands at 916, 1146, 1167, 1295, 1651, 1664, 2909, 2955, 3003 and 3146 cm$^{-1}$; and
(c) a melting point of 199 to 201° C.

4. A method for producing a crystal of 3-cyclopropyl-6-{(1R)-1-[4-(1,1-difluoroethyl)phenyl]-2-[(2R)-5-oxopyrrolidin-2-yl]ethyl}pyridin-2(1H)-one having the physical properties of the following (a) to (c):
(a) an X-ray powder diffraction pattern (Cu—Kα) showing peaks at diffraction angles 2θ of 8.5, 13.4, 19.1 and 24.5°;
(b) an infrared absorption spectrum showing characteristic absorption bands at 916, 1146, 1167, 1295, 1651, 1664, 2909, 2955, 3003 and 3146 cm$^{-1}$; and
(c) a melting point of 199 to 201° C.,
the method comprising: dissolving 3-cyclopropyl-6-{(1R)-1-[4-(1,1-difluoroethyl)phenyl]-2-[(2R)-5-oxopyrrolidin-2-yl]ethyl}pyridin-2(1H)-one represented by formula [1] in an alcohol solvent while heating, to provide a solution; thereafter, adding a water solvent to the solution; cooling the resultant solution to 5° C. or lower to yield a crystal; and
drying the obtained crystal at 60° C. or lower:

[1]

5. A pharmaceutical composition comprising, as an active ingredient, the compound, a tautomer of the compound, a pharmaceutically acceptable salt thereof, or a solvate of the compound, the tautomer thereof, or the salt thereof of claim 1, and pharmacologically acceptable carriers or diluents.

6. A method for activating glucokinase, comprising administering an effective amount of the compound according to claim 1 to a subject in need thereof.

7. The pharmaceutical composition according to claim 5, which is a hypoglycemic agent.

8. A method for treating diabetes comprising administering an effective amount of the compound according to claim 1 to a subject in need thereof.

* * * * *